United States Patent [19]

Christidis

[11] 4,156,093
[45] May 22, 1979

[54] PROCESS FOR INCREASING THE PRODUCTION OR RECOVERY YIELDS OF HEMIACETAL-ESTERS OF GLYOXYLIC ACID

[75] Inventor: Yani Christidis, Paris, France

[73] Assignee: Hoechst France, Puteaux, France

[21] Appl. No.: 886,225

[22] Filed: Mar. 13, 1978

[30] Foreign Application Priority Data

Mar. 17, 1977 [FR] France ............................... 77 08071

[51] Int. Cl.$^2$ ............................................ C07C 69/66
[52] U.S. Cl. .................................. 560/186; 560/180; 562/580; 562/587
[58] Field of Search .................... 560/186; 260/535 R; 562/579, 580, 587

[56] References Cited
U.S. PATENT DOCUMENTS 3,911,003  10/1975  Suzuki ............................ 260/535 R

FOREIGN PATENT DOCUMENTS 1004158  12/1955  Fed. Rep. of Germany.

OTHER PUBLICATIONS

Prey, V. "Die Spaltung von Phenolaethern mit Pyridiniumsalzen. . . ", Berichte der Deutschen Chemischen Gesellschaft. (1942), pp. 541–542.
Kirk–Othmer, "Encyclopedia of Chemical Technology", vol. 8, p. 326, 2nd Ed. (1966), Interscience Publ.

Primary Examiner—Bernard Helfin
Assistant Examiner—L. Hendriksen
Attorney, Agent, or Firm—Karl W. Flocks

[57] ABSTRACT

The process comprises the hot treatment at a temperature of 80° to 160° C. by an amount of 5 to 50% of 85% of phosphoric acid, of the residues resulting from the distillation of reaction media containing hemiacetal-esters under substantially anhydrous conditions. These reaction media are selected from among those resulting from the reaction of alcohols and glyoxylic acid and those resulting from the treatment of glyoxylic hemiacetal-esters with $P_2O_5$.

3 Claims, No Drawings

PROCESS FOR INCREASING THE PRODUCTION OR RECOVERY YIELDS OF HEMIACETAL-ESTERS OF GLYOXYLIC ACID

BACKGROUND OF THE INVENTION

1. Field of the Invention

The present invention relates to a process for the obtaining, with high yields and for the recovery in high proportion, of glyoxylic acid hemiacetal-esters.

2. Description of the Prior Art

Glyoxylic acid hemiacetal-esters are principally used at present for preparing the corresponding esters by the action of $P_2O_5$ (W. OROSHNIK and P. E. SPOERRI, "J. Amer. Chem. Soc." 1941, 63, 3338) and this method is only used for preparing the esters of lower alcohols. The esters of alcohols with $C_4$ and more and notably butyl glyoxylate are currently obtained by the oxidation of the corresponding tartaric esters by lead tetraacetate (Organic Syntheses, coll. vol. IV p. 124) or by periodic acid (T. R. KELLY, Th. E. SCHMIDT and J. G. HAGGERTY Synthesis, 1972, (10) 544–5). The esters of arylaliphatic alcohols can be prepared by the action of an alkali or alkaline-earth glyoxylate on an aralkyl halide (German Patent Application No. 2,403,445). In fact, it is not possible to obtain aldo-esters by direct esterification of glyoxylic acid by alcohols, although, in contradiction with all known teachings, certain authors (German patent application No. 2,241,862) describe the preparation of glyoxylic esters of $C_4$–$C_{10}$ alcohols by condensation of glyoxylic acid with the alcohol in the presence of a strong acid catalyst.

It is known that when glyoxylic acid is reacted with an alcohol in the absence of a catalyst, the glyoxylic hemiacetal-ester is essentially obtained containing a little glyoxylic ester and glyoxylic-acetal-ester, whereas in the presence of a strong acid as catalyst it is rather the acetal-ester which is formed (German Pat. Nos. 928,405 and 1,004,158). The condensation of glyoxylic acid in aqueous solution with alcohols, in the absence of a catalyst and with the elimination of water, either by prior concentration of the aqueous glyoxylic acid solution, or in the course of the reaction by azeotropic dehydration, has been in fact proposed for manufacturing glyoxylic hemiacetal-esters (German Pat. No. 1,004,158). However this process gives relatively low yields of hemiacetal-ester for alcohols of $C_4$ and more.

Accordingly it is an object of the invention to provide a process for increasing the yields of glyoxylic acid hemiacetal-esters.

It is a further object of the invention to provide an improved process for producing glyoxylic acid hemiacetal-esters of alcohols of $C_4$ and more.

It is another object of the invention to provide a process for recovering glyoxylic acid hemiacetal-esters in high proportion from media containing them.

It is another object of the invention to provide a process for producing glyoxylic acid esters in improved yields.

Other objects and advantages of the invention will be apparent from the description which follows.

Applicant has found that if the hemiacetal-esters

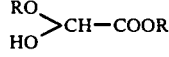

are subjected to heating under substantially anhydrous conditions, either in the course of their process of production after reaction of the glyoxylic acid OHC—COOH with a ROH alcohol, or in the course of the manufacture of aldo-esters OHC—COOR by the action of $P_2O_5$ on the hemiacetal-esters, there is formed, especially where hemiacetal-esters of alcohols of $C_4$ and more are concerned, a "bridged ketal"

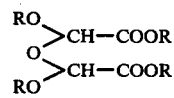

by dehydration between two hemiacetal-esters and that if, after having separated the remaining hemiacetal-esters, the resulting reaction medium is subjected to the action of a 85% phosphoric acid ($H_3PO_4$) solution, an additional amount of hemiacetal-esters is obtained.

The production of the latter can be explained by the hydrolysis of the "bridged ketal" and/or of the acetal-esters possibly present in the medium.

This discovery has been applied in the present invention and can be utilised both in the manufacture of glyoxylic hemiacetal-esters by the action of glyoxylic acid on alcohols and in the utilization of hemiacetal-esters for the manufacture of esters by the action of $P_2O_5$ on the hemiacetal-esters. Thus, therefore, in the first case the invention enables the yield of hemiacetal-esters to be considerably increased and in a second case the invention enables the recovery of the greater part of the hemiacetal-ester which has been dehydrated and not converted to aldo-ester.

GENERAL DESCRIPTION OF THE INVENTION

Thus therefore, according to the invention, there is added to the distillation residue from a reaction medium containing a hemiacetal-ester, from 5 to 50%, preferably 10 to 20% of its weight of 85% phosphoric acid and it is heated with stirring for 15 minutes to 1 hour at a temperature of 80° C. to 160° C., and then redistilled under vacuum to recover the hemiacetal-ester formed. Tests carried out with acids other than 85% phosphoric acid showed themselves to be negative. For example, with sulfuric acid, the sulfates obtained are not stable and moreover hydrolysis of the esters occurs. By means of this method of operating, there is obtained even with alcohols of $C_4$ or more, yields of hemiacetal-esters higher than 90%.

In the preparation of glyoxylic esters by the action of $P_2O_5$ on hemiacetal-esters, it is advantageous to recover the hemiacetal-ester which has not been converted into aldo-ester by collecting it by distillation after having also separated by distillation the aldo-ester formed. With hemiacetal-esters of alcohols higher than $C_4$, this is only possible by treating the distillation residue of the aldo-ester by 85% phosphoric acid under the same conditions as in the process for the preparation of hemiacetal-esters. The conversion yield is thus considerably improved.

The process according to the invention is applicable for the manufacture of all hemiacetal-esters of aliphatic alcohols, even for the hemiacetal-methyl ester, but it is particularly advantageous for hemiacetal-esters of alcohols of $C_4$ and more. In the same way, the treatment by 85% phosphoric acid of distillation residues of aldo-esters in the preparation of the latter from hemiacetal-esters is especially advantageous in the case of hemiacetal-esters of higher alcohols.

Thus as has been indicated above, the hemiacetal-esters of glyoxylic acid are used essentially for the manufacture of glyoxylic esters which constitute themselves, notably butyl glyoxylate, important starting materials for a certain number of organic syntheses. In addition, the gyloxylates of $C_4$ to $C_{10}$ alcohols can be recommended into antimicrobial formulations.

DESCRIPTION OF PREFERRED EMBODIMENTS

The following examples are given by way of illustration and are not to be regarded as in any way limiting the invention.

EXAMPLE 1

The mixture of 740 g (5 moles) of 50% aqueous glyoxylic acid solution and 1112 g (15 moles) of butanol is dehydrated by azeotropic distillation with butanol reflux into the reaction vessel. When the dehydration is finished, it is cooled, concentrated under vacuum to recover the excess butanol, then the hemiacetal-ester is distilled under 16 mm of mercury between 77° and 85° C. 622 g of a pale yellow hemiacetal-ester are obtained titrating 64% butyl glyoxylate (theory 63.7%) by vapor phase chromatography are obtained (in vapor phase chromatography : VPC under the conditions selected, the hemiacetal-ester dissociates into the aldo-ester and alcohol). To the 440 g of distillation residue is added 50 g of 85% phosphoric acid, stirred for 15 minutes at 120° C. and then it is distilled slowly under vacuum. In this way 348 g of hemiacetal-ester are recovered at 80°–84° C. under 16 mm of mercury, namely in total a yield of 95% of hemiacetal-ester with respect to the glyoxylic acid.

EXAMPLE 2

In two hours a mixture of 740 g (5 moles) of a 50% aqueous solution of glyoxylic acid and 1328 g (13 moles) of hexanol are dehydrated by azeotropic distillation, and the excess hexanol is then distilled off under vacuum and then the hemiacetal-ester (B.P.$_{20}$ = 112°–115° C.). In this way 760 g of hemiacetal-ester are obtained. The residue is stirred for 1 hour at 160° C. with 100 g of 85% phosphoric acid, and then 472 g of hemiacetal-ester are recovered by a distillation, namely in total 1232 g of hemiacetal-ester titrating 62.5% of hexyl glyoxylate (theory 60.8%) by VPC, namely a yield of 98% with respect to the glyoxylic acid.

By the treatment of 1232 g (4.87 moles) of hemiacetal-ester by $P_2O_5$, 615 g of hexyl glyoxylate are obtained ($BP_1 = 67°$ C., $BP_{1.5} = 84°$ C.), which is greenish yellow with an irritating odor, namely a yield of 76% with respect to the hemiacetal-ester utilized, of ester titrating 98% by VPC.

The residue of 680 g is stirred for 30 minutes at 120° C. with 50 g of 85% phosphoric acid, then distilled; 140 g of hemiacetal-ester titrating 64% of hexyl glyoxylate by VPC, are thus recovered.

Taking into account the hemiacetal-ester recovered, the yield of glyoxylic ester is 93%.

EXAMPLE 3

A mixture of 888 g (6 moles) of 50% aqueous solution of glyoxylic acid and 1743 g of heptanol (15 moles) are heated with stirring until complete dehydration. By distillation under reduced pressure 308 g of heptanol still containing a little water, are first collected, then 1005 g of hemiacetal-ester ($BP_{18} = 122°-123°$ C.). The distillation residue is stirred for 1 hour at 160° C. with 135 g of 85% phosphoric acid, then distilled under vacuum; in this way 548 g of hemiacetal-ester are obtained, namely in total 1553 g of hemiacetal-ester titrating 63.6% of heptyl glyoxylate by VPC, namely a yield of 96% with respect to the glyoxylic acid.

1550 g (5.73 moles) of hemiacetal-ester treated by $P_2O_5$ provides 769 g of heptyl glyoxylate ($BP_2 = 77°$ C., $BP_1 = 71°$ C.) titrating 98% by VPC.

The residue stirred for 30 minutes at 130° C. with 50 g of 85% phosphoric acid gives by distillation 291 g of hemiacetal-ester ($BP_1 = 70°$ C.—$BP_3 = 90°$ C.) titrating 70% of heptyl glyoxylate by VPC.

The yield of heptyl glyoxylate is hence 73% with respect to the hemiacetal-ester utilized and 94% taking into account the hemiacetal recovered.

EXAMPLE 4

A mixture of 740 g (5 moles) of 50% glyoxylic acid and 2050 g (11 moles) of dodecanol are dehydrated by distillation for 4 hours at atmospheric pressure without exceeding 130° C. in the mass. The excess dodecanol is then removed under vacuum and the hemiacetal-ester is distilled. 1573 g of product ($BP_{0.1} = 125°$ C. to $BP_3 = 160°$ C.) are collected, titrating 62% of dodecyl glyoxylate by VPC. To the residue cooled to 100° C. is added 100 g of 85% $H_3PO_4$, it is heated to 160° C., kept at this temperature for 15 minutes, then distilled under vacuum; in this way 183 g of hemiacetal-ester titrating 65% of dodecyl glyoxylate by VPC, are obtained, namely in total a yield of 91% with respect to the glyoxylic acid.

The treatment of about 690 g (185 moles) of hemiacetal-ester by $P_2O_5$ provides 190 g of straw yellow liquid ($BP_{0.3} = 123°-125°$ C.) titrating 64% of dodecyl glyoxylate at 35% of dodecylene by VPC separable by vacuum distillation and 197 g of liquid containing 20% of dodecyl glyoxylate and 80% of dodecylene also separable by distillation.

EXAMPLE 5

Under 18 mm of mercury, 4440 g (30 moles) of 50% glyoxylic acid are concentrated to a weight of 2395 g. After cooling 2885 g (90 moles) of methanol are added and it is kept for 3 hours at 85° C. with stirring, then cooled to 20° C. and concentrated under 50 mm of mercury and then the hemiacetal-ester is distilled. 3245 g of hemiacetal-ester are obtained. The brown residue of 340 g is heated for 30 minutes to 120°–130° C. with 50 g of 85% phosphoric acid. 195 g of hemiacetal-ester are recovered by distillation. In total 3440 g of hemiacetal-ester are obtained titrating 11% of water and 61% of methyl glyoxylate by VPC, namely a yield of 79.4% with respect to the glyoxylic acid.

Redistilled, the hemiacetal-ester is a colorless liquid of ethereal odor ($BP_{760} = 122°-124°$ C., $D_{20} = 1.206$).

It is self-evident that the present invention has only been described by way of illustration and in no limiting manner and that any useful modification can be introduced therein without departing from its scope as defined by the appended claims.

I claim:

1. In a process for producing hemiacetal-esters by the reaction of glyoxylic acid with alcohols and distillation under substantially anhydrous conditions, the improvement comprising the hot treatment of the residue resulting from said distillation at a temperature of 80° to 160° C. with an amount of 5 to 50% of 85% phosphoric acid.

2. Process according to claim 1, wherein the amount of 85% phosphoric acid is in the range of 10 to 20% by weight with respect to the medium to be treated.

3. Process according to claim 1, wherein the hemiacetal-esters are those corresponding to alcohols of $C_4$ to $C_{12}$.

* * * * *